United States Patent [19]

Eilingsfeld et al.

[11] 3,998,894

[45] Dec. 21, 1976

[54] MANUFACTURE OF 1-METHYL-3-(MONOHALOGENO)-PHENYLINDANS AND DIHALOGENO-1-METHYL-3-PHENYLINDANS

[75] Inventors: Heinz Eilingsfeld, Frankenthal; Karl Gerhard Baur; Manfred Patsch, both of Ludwigshafen; Rolf Platz, Mannheim; Hans-Georg Schecker, Ludwigshafen; Martin Fischer, Ellerstadt, all of Germany

[73] Assignee: BASF Aktiengesellschaft, Ludwigshafen, Rhine, Germany

[22] Filed: Nov. 15, 1973

[21] Appl. No.: 416,256

[30] Foreign Application Priority Data

Nov. 18, 1972 Germany .......................... 2256702
June 1, 1973 Germany .......................... 2327867
May 30, 1973 Germany .......................... 2327569

[52] U.S. Cl. ..................... 260/649 R; 204/163 R
[51] Int. Cl.² ..................... C07C 25/28; B01J 1/10; C07C 17/26
[58] Field of Search .............................. 260/649 R

[56] References Cited

UNITED STATES PATENTS 3,270,068   8/1966   Van Venrooy ................ 260/649 R
3,723,555   3/1973   Armbrust et al. ............. 260/668 F

FOREIGN PATENTS OR APPLICATIONS 2,029,026   12/1971   Germany ....................... 260/649 R

*Primary Examiner*—D. Horwitz
*Attorney, Agent, or Firm*—Johnston, Keil, Thompson & Shurtleff

[57] ABSTRACT

Manufacture of 1-alkyl-3-(monohalogeno)-phenylindans and dihalogeno-1-methyl-3-phenylindans by reaction of halogenostyrene and styrene in the presence of phosphoric acid of a certain concentration, or by reaction of halogenostyrenes in the presence of phosphoric acid of a certain concentration and of organic compounds irradiated with light of 2,000 to 8,000 A and capable of absorbing the said light, and the new dihalogeno-1-methyl-3-phenylindans and 1-methyl-3-(monohalogeno)-phenylindans. The products are starting materials for the manufacture of dyes and pesticides.

13 Claims, No Drawings

MANUFACTURE OF 1-METHYL-3-(MONOHALOGENO)-PHENYLINDANS AND DIHALOGENO-1-METHYL-3-PHENYLINDANS

The invention relates to a process for the manufacture of 1-methyl-3-(monohalogeno)-phenylindans and dihalogeno-1-alkyl-3-phenylindans by reaction of halogenostyrene and styrene in the presence of phosphoric acid of a certain concentration, or by reaction of halogenostyrenes in the presence of phosphoric acid of a certain concentration and of organic compounds irradiated with light of 2,000 to 8,000 A and capable of absorbing the said light, and the new dihalogeno-1-methyl-3-phenylindans and 1-methyl-3-(monohalogeno)-phenylindans.

It is known that styrene can be dimerized in the presence of phosphoric acid or sulfuric acid at elevated temperatures to give a mixture of 1,3-diphenylbutene-(1) and 1-methyl-3-phenylindan (J.Org. Chem., volume 19 (1954), pages 17 et seq. and volume 27 (1962), pages 1,636 et seq; J.Chem.Soc., 1964, pages 1,573 et seq; RabJohn, Organic Syntheses, Coll. Vol. IV, pages 665 et seq.). The method involves a complicated system of side reactions and secondary reactions. The first step is the dimerization of the monomeric styrene to give 1,3-diphenylbutene-(1) of which the cis and trans structural isomers are formed. This is followed by the cyclization of the trans-form to give the indan. The cis and trans forms give rise to trimers and higher polymers of styrene as further undesired by-products. All these processes prove economically unsatisfactory in commercial operation.

German Laid-Open Specification 1,950,434 discloses that styrene can be converted to 1-methyl-3-phenylindan by carrying out the reaction continuously at a concentration of less than 10 per cent by weight of styrene and more than 60 per cent by weight of 1-methyl-3-phenylindan, based on the organic phase of the two-phase reaction mixture, in the presence of phosphoric acid, sulfuric acid and/or halogenoalkanecarboxylic acids. Nuclear-monochlorinated styrenes give the corresponding dichloroindans but no significant amounts of monochloroindans.

It is an object of the present invention to provide a new process by which the new 1-methyl-3-(monohalogeno)-phenylindans and known and new dihalogeno-1-methyl-3-phenylindans can be manufactured simply and economically, in high purity and with good yields and space-time yields.

A further object of the present invention is the new dihalogeno-1-methyl-3-phenylindans and 1-methyl-3-(monohalogeno)-phenylindans themselves.

We have found that 1-alkyl-3-(monohalogeno)-phenylindans of the general formula

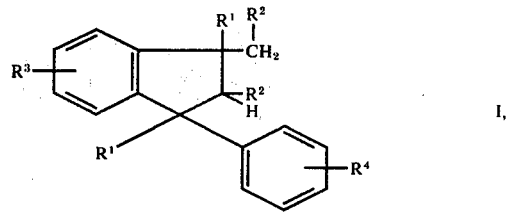

and dihalogeno-1-alkyl-3-phenylindans of the general formula

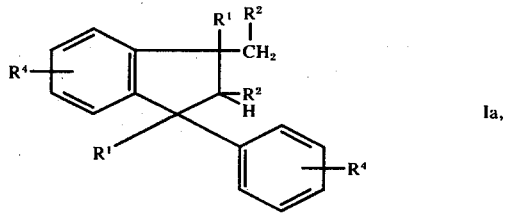

where $R^1$, $R^2$ and $R^3$ are identical or different and each is alkyl or hydrogen and $R^4$ is halogen, are obtained advantageously by reacting a mixture of styrene of the general formula

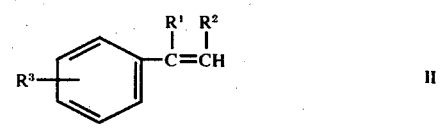

and of halogenstyrene of the general formula

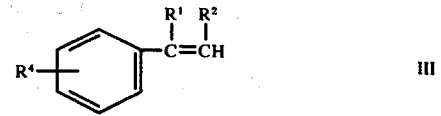

in which $R^1$, $R^2$, $R^3$ and $R^4$ have the above meanings, in the presence of phosphoric acid of at least 75 per cent strength by weight and optionally, additionally to the acid, in the presence of organic compounds irradiated with light of 2,000 to 8,000 A and capable of absorbing the said light, or reacting halogenostyrenes of the general formula

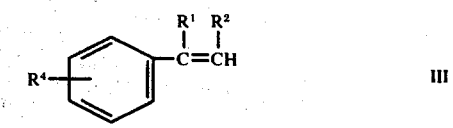

in which $R^1$, $R^2$ and $R^4$ have the above meanings as sole starting materials in the presence of phosphoric acid of at least 75 per cent strength by weight and, additionally to the acid, in the presence of organic compounds irradiated with light of 2,000 to 8,000 A and capable of absorbing the said light.

Where styrene and o-chlorostyrene are used, the reaction can be represented by the following formulae:

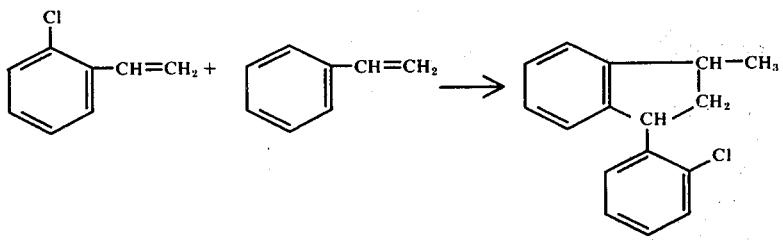

Where p-chlorostyrene is used, the reaction can be represented by the following formulae:

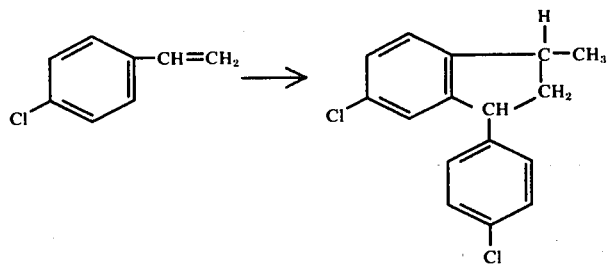

In view of the known processes, it is surprising that the process of the invention gives the new 1-alkyl-3-(monohalogeno)-phenylindans and known and new dihalogeno-1-alkyl-3-phenylindans simply and economically, in high purity and with good yield and space-time yield. These advantageous results are surprising in the light of the state of the art because heterogeneous mixtures containing a high proportion of 1-methyl-3-(monohalogeno)-phenyl-halogenoindan with one halogen atom in each of the two aromatic nuclei, of 1-methyl-3-phenyl-halogenoindan and of non-halogenated 1-methyl-3-phenylindan would have been expected.

It would also have been expected that the addition which leads to the end product would occur with more difficulty or would not occur at all if the aromatic nucleus to be substituted carries a halogen atom exerting a negative inductive effect. Furthermore, in the case of o-substituted halogenstyrenes, in contrast to unsubstituted styrene, only half the number of o-positions capable of reaction are available, that is to say purely statistically a reaction to give the end product will be less favored in the case of o-substituted styrenes than in the case of styrene. The advantageous results obtained are furthermore surprising in view of the teaching that light, in the presence or absence of sensitizers, initiates or promotes and accelerates, the polymerization of styrene to give polymeric styrenes (Houben-Weyl, Methoden der Organischen Chemie, volume XIV/1, page 769).

Preferred starting materials of the general formulae II and III and, accordingly, preferred end products I and Ia are those where $R^1$, $R^2$ and $R^3$ are identical or different and each is alkyl of 1 to 4 carbon atoms or hydrogen and $R^4$ is bromine or especially chlorine. The starting materials III can be m-halogenostyrenes and in particular p-halogenostyrenes or o-halogenostyrenes. The radicals $R^1$ and/or $R^2$ of starting material II can optionally also differ from the radical $R^1$ and/or $R^2$ of starting material III.

Examples of starting materials II which can be used are styrene, p-methylstyrene, α-methylstyrene, β-propylstyrene, α,β-dimethylstyrene and α-isobutylstyrene. Examples of suitable starting materials III are o-chlorostyrene, p-chlorostyrene, m-chlorostyrene, o-bromostyrene, m-bromostyrene and p-bromostyrene, and α-methylstyrene, β-propylstyrene, α,β-dimethylstyrene and α-isobutylstyrene mono-substituted by chlorine or bromine in the o-, m- or p-position of the phenyl ring. Starting material II is generally reacted with starting material III in approximately stoichiometric amounts though optionally either starting material can be used in an excess of up to 10 moles, preferably of up to 3 moles, over the stoichiometric amount, per mole of the other starting material.

As a rule, the reaction is carried out at a temperature from 10° to 150° C, preferably from 20° to 50° C, in the case of the reaction of starting material II and starting material III and preferably from 40° to 100° C, especially 40° to 80° C, in the case of the reaction involving starting materials III only, without pressure or under super-atmospheric pressure, for example at 0.3 to 3 atmospheres, and continuously or batchwise. If desired, organic solvents which are inert to the reaction, for example aliphatic hydrocarbons of boiling point preferably from 30° to 180° C, such as ligroin, n-pentane, n-heptane, hexane or nonane, α-pinene, pinane, o-, m- and p-cymene, gasoline fractions boiling within the above-mentioned boiling range, petroleum ether, 2,2,4-trimethylpentane, 2,2,3-trimethylpentane, 2,3,3-trimethylpentane or octane, cycloaliphatic hydrocarbons such as tetrahydronaphthalene or cyclohexane, and chlorinated hydrocarbons such as chlorobenzene, dichlorobenzene, chloroalkylbenzenes such as p-chloroethylbenzene, o-chloro-isopropylbenzene, tetrachloroethylene, tetrachloroethane, carbon tetrachloride, chloroform, trichloroethylene, pentachloroethane, cis-dichloroethylene or 1,2-dichloroethane, or their mixtures, can be present in the reaction. Suitable amounts of solvent to use are from 50 to 150 per cent by weight, based on starting material III.

The phosphoric acid is used anhydrous or mixed with water, in the form of phosphoric acid of strength at least 75 per cent by weight, preferably 85 to 100 per cent by weight and especially 90 to 100 per cent by weight. 0.8 to 5, especially 2 to 4, parts of acid (taken as 100% strength) can be used per part of starting material III. Metaphosphoric acid, pyrophosphoric acid or, especially, orthophosphoric acid can be used, for example. The phosphoric acid can also be in the form of a polyphosphoric acid, for example containing from 72 to 88 per cent by weight of $P_2O_5$; equally, it is possible to add phosphorus pentoxide, preferably in the amounts corresponding to polyphosphoric acids, alongside phosphoric acid of the abovementioned concentrations. 89 to 95 per cent strength by weight phosphoric acid is of particular interest because of the yield of end product, which can decline somewhat, depending on the structure of the starting material, if more highly concentrated phosphoric acids are used. If phosphoric acids of less than 85 per cent strength by weight are used, the yield of end product decreases with decreasing acid concentration and in the case of the reaction of starting materials II and III the yield of dihalogenated 1-methyl-3-phenylindan and especially the yield of non-halogenated 1-methyl-3-phenylindan increases.

The yield of monohalogeno-1-alkyl-3-phenylindan can therefore be altered by varying the reaction conditions; which can under certain circumstances be of value in industrial operation. The unsubstituted 1-methyl-3-phenylindans and dihalogeno-1-methyl-3-phenylindans obtained as by-products, which are of industrial importance as anthraquinone intermediates, can, by such variation, be produced together, in larger or smaller amount, depending on requirements. The dichloro-1-alkyl-3-phenylindans obtained from such a mixed dimerization process retain very little or hardly any open-chain dimers and can therefore be converted with particularly good yields into dichloroanthraquinone.

In some cases it is advantageous to add a polymerization inhibitor, for example to increase the yield of end product (relative to converted monohalogenostyrene III). The polymerization inhibitors used can be any desired substances which prevent or greatly retard the polymerization of monomers and thus act as stabilizers for the monomers. The substances can be gaseous, solid or liquid, substances which inhibit the polymerization of vinyl compounds being preferred. The following substances are advantageously used as inhibitors: thioureas, for example thiourea, methylthiourea, phenylthiourea, N,N-diphenylthiourea, N,N'-diphenylthiourea, N-methyl-N-(p-toluyl)-thiourea, S-benzyl-N-phenylisothiouronium picrate, S-methyldithiobuiret hydrochloride, phenylmethylthiourea, 2,4-dimethoxyphenylthiourea, 4-methoxy-phenylthiourea, di-n-butyl-thiourea, 1-benzoyl-thiosemicarbazide and dithiobuiret; phenols, thiophenols and their ethers, for example hydroquinone monomethyl ether, 4-butyl pyrocatechol, N-benzyl-p-aminophenol and o-aminophenol; heterocyclic sulfur compounds containing sulfur as a substituent or in a side chain on the heterocyclic ring, for example 2-mercaptobenzimidazole, 2-mercapto-4-anilino-quinazoline or 2-thiocyanatomethylbenzimidazole, or containing a sulfur atom in the heterocyclic ring, for example phenthiazine, thionaphthene, 2-mercapto-benzthiazole, 2-aminobenzthiazole, 3-amino-benzisothiazole, 2-methylbenzthiazole, diphenylene sulfide, 2,5-dimercapto-1,3,4-thiadiazole and tetramethylenetrithione; substituted aromatic amines, for example N-phenyl-α-naphthylamine and N-phenyl-β-naphthylamine; nitroso compounds, for example o-, p- and m-nitrosophenol, N-nitrosophenylhydroxylamine ammonium salt (cupferron), nitrogen monoxide and dinitrogen tetroxide; organic phosphorus compounds, for example triphenylphosphine and triphenylphosphite; thiocarboxylic acid amides, for example thioacetamide, anthranilic acid thiamide, 2-amino-5-nitrothiobenzamide, 2-amino-3-bromo-5-nitrothiobenzamide, 2-amino-3,5-dibromothiobenzamide and thiobenzamide; and mixtures thereof. In general, from $10^{-5}$ to $10^{-2}$, preferably from $10^{-4}$ to $10^{-3}$, mole of polymerization inhibitor is employed per mole of starting material III.

Where appropriate, further acids are employed additionally to phosphoric acid, in particular to facilitate separation of the reaction mixture into an aqueous phase and an organic phase when working up. This process is also particularly advantageous for the manufacture of dihalogen compounds. Inorganic acids, organic acids or Lewis acids can be used as such acids. A definition of Lewis acids is to be found in Ullmanns Encyklopadie der technischen Chemie, volume 15, pages 2 to 3, and volume 18, pages 66 to 67. Instead of monobasic acids, equivalent amounts of polybasic acids can be employed. Examples of suitable acids are perchloric acid, nitric acid, sulfonic acids such as benzene sulfonic acid and p-toluenesulfonic acid, acids containing boron such as boric acid and hydrofluoboric acid, aliphatic carboxylic acids such as monochloroacetic acid, dichloroacetic acid and trichloroacetic acid, oxalic acid, formic acid, cyanoacetic acid, acetic acid, propionic acid, butyric acid, isobutyric acid, glycolic acid, lactic acid, tartaric acid, citric acid, adipic acid and maleic acid, cycloaliphatic, araliphatic and aromatic carboxylic acids such as benzoic acid, cyclohexanecarboxylic acid, phenylacetic acid, phthalic acid and p-toluic acid, Lewis acids such as the adducts of ethanol and boron fluoride, boron chloride and zinc chloride, complex compounds of boron trifluoride with nitrogen compounds such as ammonia, amines, or nitric oxide, or with water, for example in the form of boron trifluoride dihydrate, or with ethers, for example dimethyl ether, and substances which form such complex compounds under the reaction conditions, for example alkali metal phosphates, alkali metal fluorides and boron trifluoride in the acid reaction mixture, or substances which contain such compounds, for example oxofluoboric acids or alkali fluoborates, boron trichloride complex compounds with phosphorus trichloride and phosphorus oxychloride, and halides of metals of groups 2 to 6 of the Periodic System, such as zinc chloride, boron chloride, aluminum chloride, tin chlorides, titanium chloride, antimony chlorides, bismuth chloride, molybdenum chloride, tungsten chlorides, aluminum bromide and boron trifluoride, and boron fluorideacetic acid, -diacetic acid and -phosphoric acid.

It is also possible to use substances which form such additional acids under the reaction conditions, such as $SO_3$, $POCL_3$, $AlCl_3$, $ZnCl_2$, $SO_2Cl_2$ or $CF_3SO_3H$. Preferred additional acids are sulfuric acid and nitric acid. The acids can be employed in a concentrated form, mixed with one another and/or mixed with one of the solvents mentioned earlier. The additional acid is preferably used in amounts from 0.05 to 0.5 mole per mole of starting substance III.

Preferred additional acids or additives, especially when manufacturing the dihalogen compounds, are phosphorus pentoxide, phosphorus oxychloride, phosphorus pentachloride, thionyl chloride and polyphosphoric acid, Lewis acids such as boron trifluoride, aluminum chloride or zinc chloride, and strong proton acids such as sulfuric acid, nitric acid or α-halogenoalkanecarboxylic acids or α-halogenoalkanesulfonic acids with 1 to 5 carbon atoms, especially α-chloroalkanecarboxylic acids or α-chloroalkanesulfonic acids with the said number of carbon atoms, preferably in the anhydrous form. Examples of α-halogenoalkanecarboxylic acids or α-halogenoalkanesulfonic acids are dichloroacetic acid, trichloroacetic acid, trichloromethanesulfonic acid or trifluoromethanesulfonic acid. Polyphosphoric acid, phosphorus oxychloride, thionyl chloride, boron trifluoride and aluminum chloride are particularly preferred as additional proton acids or Lewis acids.

An advantageous embodiment of the process is based on the fact that compounds which absorb light of 2,000 to 8,000 A are activated quite specifically by irradiation with such light and, surprisingly, promote the dimerization and at the same time the cyclization of the halogenostyrenes or of halogenostyrenes and styrenes to the corresponding indans. The compounds which can be activated by light can be gaseous, solid or liquid. It is convenient if the organic compounds concerned at the same time act as polymerization inhibitors. Light absorbing substances which prevent or greatly retard the polymerization of monomers and thus act as stabilizers for the monomers, can with advantage be used as the organic compounds, and those which inhibit the polymerization of vinyl compounds are preferred. It is also possible to employ light-absorbing organic compounds, for example nitrobenzene, and additionally polymerization inhibitors, for example phenylthiourea.

The following organic compounds can be used with advantage: thioureas, for example thiourea, methylthiourea, phenylthiourea, N,N-diphenylthiourea, N,N'-diphenylthiourea, N-methyl-N-(p-toluyl)-thiourea, S-benzyl-N-phenylisothiouronium picrate, S-methyl-dithiobiuret hydrochloride, phenylmethylthiourea, 2,4-dimethoxy-phenylthiourea, 4-methoxy-phenylthiourea, di-n-butylthiourea, 1-benzoyl-thiosemicarbazide and dithiobiuret, phenols, thiophenols and their ethers, for example hydroquinone monomethyl ether, 4-butylpyrocatechol, N-benzyl-p-aminophenol and o-aminophenol, heterocyclic sulfur compounds, with sulfur as the substituent or in a side chain on the heterocyclic ring, for example 2-mercaptobenzimidazole, 2-mercapto-4-anilinoquinazoline or 2-thiocyanomethylbenzimidazole, or with a sulfur atom in the heterocyclic ring, for example phenothiazine, thionaphthene, 2-mercaptobenzthiazole, 2-aminobenzthiazole, 3-aminobenzisothiazole, 2-methylbenzthiazole diphenylenesulfide, 2,5-dimercapto-1,3,4-thiadiazole, thianthrene, leuco-methylene blue and tetramethylenetrithione, substituted aromatic amines, for example diphenylamine, m-acetaminodiphenylamine, N-phenyl-α-naphthylamine, N-phenyl-β-naphthylamine and p-isopropylamino-diphenylamine, aromatic hydrazines, for example o-, p- and m-nitrosophenol, N-nitrosophenylhydroxylamine ammonium salt (cupferron), nitrogen monoxide and dinitrogen tetroxide, organic phosphorus compounds, for example triphenylphosphine and triphenylphosphite, thiocarboxylic acid amides, for example thioacetamide, anthranilic acid thiamide, 2-amino-5-nitrothiobenzamide, 2-amino-3-bromo-5-nitrothiobenzamide, 2-amino-3,5-dibromothiobenzamide and thiobenzamide, aromatic nitro compounds, for example nitrobenzene, m-dinitrobenzene, m-nitroaniline, m-nitrophenol and nitroanthraquinone, quinones, for example p-benzoquinone, anthraquinone, 2,3,4,5-tetramethylquinone, toluquinone, chloranil and naphthoquinone, aromatic ketones, for example benzophenone, and appropriate mixtures. In general, from $10^{-5}$ to $10^{-2}$, advantageously from $10^{-4}$ to $10^{-3}$, and preferably from 0.0005 to 0.001 mole, of organic compound are used per mole of starting material II.

The irradiation of the light-absorbing compounds with light (photoactivation) can be effected during the dimerization of the styrene, for example by irradiating the reaction vessel with light, or before the reaction, for example by irradiating the substances which can be photoactivated, without a solvent or, advantageously, in solution. In a particularly simple economical embodiment, the halogenostyrene compound or styrene compound envisaged for the dimerization, or the catalyst, for example phosphoric acid, is used as the solvent for such solutions.

Light soutces which emit light from 2,000 to 8,000 A, preferably from 2,500 to 4,500 A, can be used for the photoactivation. Advantageous economical utilization of the light energy is achieved if the principal emission of the light source falls within the range of the absorption bands of the particular organic compounds used. If the compounds are to be photoactivated during the reaction, or are irradiated prior to the reaction using a halogenostyrene or styrene as the solvent, wavelengths below 2,900 A should preferably be eliminated with a glass filter. Light sources which can be used include sunlight or artificial light, for example from tungsten lamps, xenon lamps, mercury arc lamps, graphite arc lamps, carbon arcs and fluorescent lamps. The irradiation provided is preferably 0.2 to 10,000 watt hours, preferably 2 to 1,000 watt hours, and especially 10 to 200 watt hours, of light per kilogram of starting material III. The light source can also be introduced into the reaction chamber, for example by using an immersed lamp. The light-absorbing organic compounds can advantageously be irradiated in a continuous flow reactor, whilst if a batch method is used they can be irradiated in individual batches. If the irradiation is carried out continuously or intermittently during the reaction, it is desirable to commence and terminate the irradiation simultaneously with the reaction. In batch processes the irradiation can, however, also be stopped before completion of the dimerization. If the irradiation is carried out separately, irradiation times of, for example, 5 to 120 minutes, prove suitable. If the irradiation is carried out simultaneously, the reaction action is carried out without pressure or under superatmospheric pressure, continuously or batchwise, and in general at the abovementioned temperatures. If the irradiation of the organic compound or of its solution in, for example, one of the abovementioned solvents, is carried out prior to the reaction, suitable irradiation temperatures are from 15° to 35° C. It is also possible, if the continuous or intermittent irradiation of the organic compound, optionally together with polymerization inhibitor, solvent and/or catalyst, is carried out separately from the reaction, to effect this irradiation shortly before the compound enters the reaction chamber; for example, the substances which can be photoactivated, dissolved in the halogenostyrene or styrene fed to the reaction, are passed in front of an irradiation lamp before entering the reaction chamber.

The compound activated by light before or during the reaction can be fed to the reaction by any desired method, for example mixed with the starting material III, the starting material II, the solid catalyst and/or the inhibitor, if any, or in solution or suspension in the liquid catalyst, or as a separate additive. When the end product is isolated, the photoactivated compound can, depending on its structure, be isolated from the organic phase and re-used, or, in the case of acid-soluble compounds, be recycled, together with the acid, to the reaction stage.

The reaction can be effected as follows: a mixture of starting materials II and III, or starting material III alone, phosphoric acid and, where relevant, the compound irradiated with light before or during the reaction, polymerization inhibitor, additional acid and/or solvent is kept at the reaction temperature for 2 to 8 hours. The end product is then isolated from the reaction mixture by conventional methods, for example by fractional distillation of the organic phase of the mixture. The following two methods are examples of how the reaction can be effected: phosphoric acid and, where relevant, the compound irradiated with light before or during the reaction, and the additives, are first introduced into a reactor. The starting material III or a mixture of starting materials II and III, optionally mixed with polymerization inhibitor and solvent, is added slowly, whilst stirring vigorously. If a batch method is used, the phases of the reaction mixture are separated after completion of the addition, and the organic phase is fractionated. In a continuous method, the phases are separated in an attached separator and the aqueous phase is recycled to the reactor. In a second method, the starting material III is suspended in phosphoric acid and optionally the abovementioned additives by vigorous stirring in a reactor. The concentration of phosphoric acid and the temperature must be so chosen that no noticeable dimerization or polymerization of the halogenostyrene III occurs; for example the acid concentration should be less than 90 per cent by weight and the temperature can be 35° C. The starting material II, optionally together with inhibitor and solvent, is then added. The phases of the reaction mixture are then separated and the organic phase is fractionated.

A further advantageous embodiment of the reaction is the following: the starting materials are reacted in a stirred apparatus or in a stirred cascade at the reaction temperature, in the presence of phosphoric acid and, where relevant, the compound irradiated with light before or during the reaction and the additives, with thorough mixing, the power input for stirring preferably being from 5 to 10 kW/m$^3$. Appropriate amounts of starting material and reactants are continuously introduced, and appropriate amounts of reaction mixture withdrawn, to maintain the abovementioned concentrations of starting material and additives in the organic phase of the mixture throughout the entire reaction time. The dwell time of the reaction mixture in the reaction chamber is in general 10 to 30 minutes. The mixture of the reactants can initially be prepared at the reaction temperature or be prepared at a lower temperature and then brought to the reaction temperature. In the stirred cascade, the individual stirred vessels can be kept at different reaction temperatures. The portion of the reaction mixture which is withdrawn continuously is passed to the phase separation stage. The aqueous phase which has been separated off and which contains the phosphoric acid can be reused directly for the reaction. The acid can, however, also be processed by conventional methods, for example by filtration, centrifuging, distillation or extraction. In the cascade of stirred kettles, it is possible either for each kettle to have its own acid loop or for all the kettles to have a shared loop. In the former case it is possible, for example, to vary the concentration of acid from kettle to kettle. The end product is isolated from the organic phase by conventional methods, for example by distillation.

Analogously, it is possible to use as the reactor any apparatus in which the starting materials are brought into intimate contact with acid and additives, for example a bubble column, a cascade reactor or packed columns, sieve plate columns, Oldershaw columns, glass plate columns, bubble cap columns or valve plate columns. The liquid styrene II or III used as the starting material is converted in the reactor, at the reaction temperature, in countercurrent to, or cocurrent with, the other starting material and the phosphoric acid, where appropriate together with the additives. Where columns are used, the reaction mixture is advantageously passed continuously through the reactor, an appropriate liquid throughput being between 10 and 100 $m^3$ per $m^2$ of column cross-section per hour.

The compounds which can be manufactured by the process of the invention are valuable starting materials for the manufacture of dyes and pesticides. 1-methyl-3-monochlorophenylindans are important starting materials for the synthesis of 1-chloroanthraquinone and 2-chloroanthraquinone whilst the dihalogeno-1-methyl-3-phenylindans are used for the synthesis of corresponding dihalogenoanthraquinones, especially dichloroanthraquinones. They can be oxidized with nitrogen dioxide in the presence of selenium dioxide to give the corresponding monochlorobenzoylbenzoic acid or the dichloro compound, and these compounds are then cyclized with sulfuric acid monohydrate to give chloroanthraquinone or the corresponding dichloroanthraquinone. Regarding the applications of monohalogenoanthraquinones and dihalogenoanthraquinones, reference may be made to Ullmanns Encyklopadie der technischen Chemie, volume 3, pages 674 et seq.

The parts specified in the Examples which follow denote parts by weight.

EXAMPLE 1

A mixture of 115 parts of o-chlorostyrene and 35 parts of o-chloroethylbenzene is added to 652 parts of 89 per cent strength by weight aqueous phosphoric acid at 40° to 45° C whilst stirring vigorously. A mixture of 90 parts of styrene, 115 parts of o-chlorostyrene and 35 parts of o-chloroethylbenzene is added to the resulting emulsion at a temperature of 40° to 45° C over 5 hours. After completion of the addition, the mixture is stirred for a further 2 hours at 40° to 45° C. The organic phase is separated off, washed with 200 parts of 3 per cent strength by weight sodium hydroxide solution and fractionated. 24.9 parts of 1-methyl-3-phenylindan (b.p. 145° to 146° C (10 mm)), 63.1 parts of 1-methyl-3-(o-chloro)-phenylindan (b.p. 165° to 168° C (10 mm), $n_D^{25}$: 1.5890) and 31 parts of 1-methyl-3-(o-chloro)-phenyl-7-chloroindan (b.p. 195° to 200° C (10 mm)) are isolated.

EXAMPLE 2

A mixture of 90 parts of styrene, 230 parts of o-chlorostyrene and 70 parts of o-chloroethylbenzene is added to 700 parts of 92 per cent strength by weight phosphoric acid at 35° to 40° C over 5 hours, whilst stirring vigorously. The mixture is stirred for a further 2 hours at 35° to 40° C and the organic phase is then separated off and washed with 200 parts of 3 per cent strength by weight sodium hydroxide solution. Fractional distillation at 10 mm Hg gives 25.5 parts of 1-methyl-3-phenylindan, 108 parts of 1-methyl-3-(o-chloro)-phenylindan (b.p. 165° to 168° C (10 mm), $n_D^{25}$: 1.5890) and 4.5 parts of 1-methyl-3-(o-chloro)-phenyl-7-chloroindan (b.p. 195° to 200° C (10 mm)).

EXAMPLE 3

A mixture of 115 parts of o-chlorostyrene and 35 parts of o-chloroethylbenzene is added to a mixture of 652 parts of 78 per cent strength by weight phosphoric acid and 20 parts of sulfuric acid monohydrate at 30° to 35° C, whilst stirring vigorously. A mixture of 90 parts of styrene, 115 parts of o-chlorostyrene and 35 parts of o-chloroethylbenzene is then added at 30° to 35° C over 5 hours. After completion of the addition, the mixture is stirred for a further 2 hours and the organic phase is separated off and washed with 200 parts of 3 per cent strength by weight sodium hydroxide solution. Fractional distillation at 10 mm Hg gives 25 parts of 1-methyl-3-phenylindan, 30 parts of 1-methyl-3-(o-chloro)-phenylindan (b.p. 165° to 168° C (10 mm), $n_D^{25}$: 1.5890) and 28 parts of 1-methyl-3-(o-chloro)-phenyl-7-chloroindan (b.p. 195° to 200° C (10 mm)).

EXAMPLE 4

A mixture of 90 parts of styrene, 174 parts of o-chlorostyrene and 126 parts of o-chloroethylbenzene is added to 680 parts of 90 per cent strength by weight phosphoric acid at 35° to 40° C over 5 hours, whilst stirring vigorously. The emulsion is stirred for a further 2 hours at 35° to 40° C. The organic phase is separated off and washed with 200 parts of 3 per cent strength by weight sodium hydroxide solution. Fractional distillation at 10 mm Hg gives 36 parts of 1-methyl-3-phenylindan, 74 parts of 1-methyl-3-(o-chloro)-phenylindan (b.p. 165° to 168° C (10 mm), $n_D^{25}$: 1.5890) and 23 parts of 1-methyl-3-(o-chloro)-phenyl-7-chloroindan (b.p. 195° to 200° C (10 mm)).

EXAMPLE 5

A mixture of 90 parts of styrene, 156 parts of o-chlorostyrene and 114 parts of o-chloroethylbenzene is added to an emulsion of 680 parts of 90 per cent strength by weight phosphoric acid and 150 parts of o-dichlorobenzene at 35° to 40° C over 5 hours, whilst stirring vigorously. The mixture is stirred for a further 2 hours at 35° to 40° C and the organic phase is separated off and washed with 200 parts of 3 per cent strength by weight sodium hydroxide solution. Fractional distillation at 10 mm Hg gives 34 parts of 1-methyl-3-phenylindan, 71 parts of 1-methyl-3-(o-chloro)-phenylindan (b.p. 165° to 168° C (10 mm), $n_D^{25}$: 1.5890) and 23 parts of 1-methyl-3-(o-chloro)-phenyl-7-chloroindan (b.p. 195° to 200° C (10 mm)).

EXAMPLE 6

A mixture of 90 parts of styrene, 217 parts of o-chlorostyrene and 83 parts of o-chloroethylbenzene is added to 722 parts of 94 per cent strength by weight phosphoric acid at 35° to 40° C over 5 hours, whilst stirring vigorously. The mixture is then stirred for a further 2 hours at 35° to 40° C and the organic phase is separated off and washed with 200 parts of 3 per cent strength by weight sodium hydroxide solution. Fractional distillation gives 31 parts of 1-methyl-3-phenylindan and 140 parts of 1-methyl-3-(o-chloro)-phenylindan (b.p. 165° to 168° C (10 mm), $n_D^{25}$: 1.5890).

EXAMPLE 7

A mixture of 90 parts of styrene, 182 parts of o-chlorostyrene, 118 parts of o-chloroethylbenzene and 0.5 part of phenothiazine is added to 600 parts of 100 per cent strength by weight phosphoric acid at 35° to 40° C over 5 hours. After completion of the addition, the mixture is stirred for one hour at 35° to 40° C. The organic phase is separated off, washed with 200 parts of 3 per cent strength by weight sodium hydroxide solution and fractionated at 10 mm Hg. 19 parts of 1-methyl-3-phenylindan, 120 parts of 1-methyl-3-(o-chloro)-phenylindan (b.p. 165° to 168° C (10 mm), $n_D^{25}$: 1.5890) and 22 parts of 1-methyl-3-(o-chloro)-phenyl-7-chloroindan (b.p. 195° to 200° C (10 mm)) are isolated.

EXAMPLE 8

A mixture of 90 parts of styrene, 234 parts of p-chlorostyrene and 66 parts of p-chloroethylbenzene is added to 722 parts of 93 per cent strength by weight phosphoric acid at 35° to 40° C over 5 hours. After a further 2 hours at 35° to 40° C the organic phase is separated off and washed with 200 parts of 3 per cent strength by weight sodium hydroxide solution. Fractional distillation gives 16 parts of 1-methyl-3-phenylindan, 78 parts of 1-methyl-3-(p-chloro)-phenylindan (b.p. 166° to 170° C (10 mm), $n_D^{25}$: 1.5869) and 13 parts of 1-methyl-3-(p-chloro)-phenyl-5-chloroindan (b.p. 197° to 204° C (10 mm)).

EXAMPLE 9

A solution containing 90 parts of styrene, 174 parts of m-chlorostyrene and 126 parts of m-chloroethylbenzene is added to 722 parts of 93 per cent strength by weight phosphoric acid at 35° to 40° C over 5 hours. After completion of the addition, the emulsion is stirred for 2 hours at 35° to 40° C. The organic phase is separated off and washed with 200 parts of 3 per cent strength by weight sodium hydroxide solution. Fractional distillation gives 27 parts of 1-methyl-3-phenylindan, 71 parts of 1-methyl-3-(m-chloro)-phenylindan (b.p. 168° to 172° C (10 mm), $n_D^{25}$: 1.5872) and 23 parts of 1-methyl-3-(m-chloro)-phenyl-6-chloroindan (b.p. 197° to 204° C (10 mm)).

EXAMPLE 10

A mixture of 90 parts of styrene, 183 parts of o-chlorostyrene and 117 parts of o-chloroethylbenzene is added to a mixture of 722 parts of 93 per cent strength by weight phosphoric acid and 7.5 parts of 65 per cent strength by weight nitric acid at 35° to 40° C over 5 hours. The emulsion is stirred for a further 2 hours at 35° to 40° C and the organic phase is then separated off and washed with 200 parts of 3 per cent strength by weight sodium hydroxide solution. Fractional distillation at 10 mm Hg gives 26 parts of 1-methyl-3-phenylindan and 148.5 parts of 1-methyl-3-(o-chloro)-phenylindan (b.p. 165° to 168° C (10 mm), $n_D^{25}$: 1.5890).

EXAMPLE 11

1 part of phenothiazine is added to 375 parts by volume of phosphoric acid (95% strength by weight) at 25° C, in a stirred vessel. The mixture is irradiated for 10 minutes with a mercury vapor lamp (15 watt hours per kilogram of styrene II and III) whilst passing 2,000 parts of air through it. A mixture of 52 parts of styrene, 78 parts of o-chlorostyrene and 42 parts of o-chloroethylbenzene is then added to the irradiated solution over 3 hours at a temperature of 38° C. After completion of the addition, the mixture is stirred for a further hour at 38° C. The organic phase is separated off, washed with 200 parts of 5 per cent strength by weight sodium hydroxide solution and fractionated. 13.8 parts of 1-methyl-3-phenylindan (b.p. 145° to 146° C (10 mm)), 85 parts of 1-methyl-3-(o-chloro)-phenylindan (b.p. 165° to 168° C (10 mm), $n_D^{25}$: 1.5890) and 5 parts of 1-methyl-3-(o-chloro)-phenyl-7-chloroindan (b.p. 195° to 200° C (10 mm)) are isolated.

EXAMPLE 12

A mixture of 375 parts of phosphoric acid (95% strength by weight) and 1 part of phenothiazine is irradiated analogously to Example 11 for 30 minutes. The reaction is effected analogously to Example 11 and fractional distillation gives 13 parts of 1-methyl-3-phenylindan, 85.5 parts of 1-methyl-3-(o-chloro)-phenylindan (b.p. 165° to 168° C (10 mm), $n_D^{25}$: 1.5890) and 7 parts of 1-methyl-3-(o-chloro)-phenyl-7-chloroindan (b.p. 195° to 200° C (10 mm)).

EXAMPLE 13

A mixture of 375 parts of phosphoric acid (95% strength by weight) and 0.9 part of phenylthiourea is irradiated for 10 minutes analogously to Example 11. The reaction is effected analogously to Example 11 and fractional distillation gives 14 parts of 1-methyl-3-phenylindan, 80 parts of 1-methyl-3-(o-chlorophenyl)-indan (b.p. 165° to 168° C (10 mm)) and 8 parts of 1-methyl-3-(o-chlorophenyl)-7-chloroindan.

EXAMPLES 14 TO 17

The results listed in the table which follows are obtained analogously to Example 13.

EXAMPLE 18

A mixture of 375 parts of phosphoric cid (95% strength by weight) and 1 part of phenothiazine is irradiated for 10 minutes analogously to Example 11. A mixture of 52 parts of styrene, 69 parts of p-chlorostyrene and 61 parts of p-chloroethylbenzene is added to the irradiated solution over 3 hours at 35° to 40° C. After completion of the addition, the mixture is stirred for a further hour at 40° C. The organic phase is separated off and washed with 200 parts of 5 per cent strength by weight sodium hydroxide solution, and fractional distillation gives 18 parts of 1-methyl-3-phenylindan and 72 parts of 1-methyl-3-(p-chlorophenyl)-indan (b.p. 151° to 155° C (4 mm), $n_D^{25}$: 1.5869).

EXAMPLE 19

A mixture of 375 parts of phosphoric acid (95% strength by weight) and 1 part of phenothiazine is irradiated for 10 minutes analogously to Example 11. A mixture of 52 parts of styrene, 76 parts of α-methyl-o-chlorostyrene and 94 parts of o-chloro-isopropylbenzene is added to the irradiated solution over 4 hours at 35° to 40° C. After completion of the addition, the mixture is stirred for a further hour at 40° C. The organic phase is separated off and washed with 150 parts of 5 per cent strength by weight sodium hydroxide solution, and fractional distillation gives 20 parts of 1-methyl-3-phenylindan and 68 parts of 1,3-dimethyl-3-(o-chlorophenyl)-indan (b.p. 147° to 152° C (0.4 mm)).

EXAMPLE 20

200 parts of 95 per cent strength by weight aqueous phosphoric acid containing 0.9 part of diphenylamine are irradiated for 10 minutes at 25° C with ultraviolet light (mercury vapor lamp, with 15 watt hours per kilogram of halogenostyrene III), whilst passing 2,000 parts of air through the mixture. 126 parts of sulfuric acid monohydrate are then added followed slowly by a mixture of 133 parts of o-chlorostyrene and 85 parts of o-chloroethylbenzene, which is added over 3 hours at 50° to 55° C. The organic phase is separated off and fractionated by distillation. 110 parts (= 82.7% of theory) of 1-methyl-3-(o-chlorophenyl)-7-chloroincan of b.p. 150° to 167° C (0.3 mm Hg) are obtained.

EXAMPLE 21

The reaction is carried out analogously to Example 20, with p-chlorostyrene instead of o-chlorostyrene. 110 parts (= 82.7% of theory) of 1-methyl-3-(p-chlorophenyl)-5-chloroindan of b.p. 148° to 156° C (0.15 mm Hg) are obtained.

EXAMPLE 22

200 parts of 98 per cent strength by weight aqueous phosphoric acid, containing 0.9 part of phenothiazine, are irradiated for 10 minutes at 25° C with ultraviolet light (mercury vapor lamp, with 15 watt hours per kilogram of halogenostyrene III), whilst passing 2,000 parts of air through the mixture. 50 parts of 98 per cent strength by weight aqueous phosphoric acid and 23 parts of boron trifluoride are added. A solution of 133 parts of o-chlorostyrene and 85 parts of o-chloroethylbenzene is added to the mixture at 50 to 55° C over 3 hours. 111 parts (= 83.5% of theory) of 1-methyl-3-(o-chlorophenyl)-7-chloroindan of b.p. 150° to 167° C (0.3 mm Hg) are obtained analogously to Example 20.

| Example | Compound irradiated with light (parts) | Yield of 1-methyl-3-phenylindan (parts) | Yield of 1-methyl-3-(o-chlorophenyl)-indan (parts) | Yield of 1-methyl-3-(o-chlorophenyl)-7-chloroindan (parts) |
|---|---|---|---|---|
| 14 | 0.9 Thianthrene | 16 | 82 | 4 |
| 15 | 0.9 Diphenylamine | 13.5 | 84 | 5 |
| 16 | 0.9 Hydrazobenzene | 14 | 82 | 5 |
| 17 | 0.75 Diphenylamine 0.45 p-benzoquinone | 13 | 81 | 6 |

EXAMPLE 23

200 parts of 98 per cent strength by weight aqueous phosphoric acid containing 0.9 part of phenylthiourea are irradiated for 10 minutes at 25° with ultraviolet light (mercury vapor lamp, with 15 watt hours per kilogram of halogenostyrene III) whilst passing 2,000 parts of air through the mixture. 70 parts of phosphorus oxychloride are added followed by a mixture of 120 arts of p-chlorostyrene and 97 parts of o-chloroethylbenzene added over 3 hours. Distillation of the organic phase gives 97 parts (= 80.7% of theory) of 1-methyl-3-(p-chlorophenyl)-5-chloroindan of b.p. 148° to 156° C (0.15 mm).

We claim:

1. A process for the manufacture of a 1-alkyl-3-(monohalogeno)-phenylindan of the formula

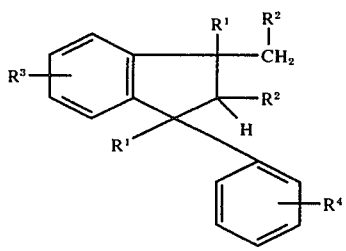

and a dihalogeno-1-methyl-3-phenylindan of the formula

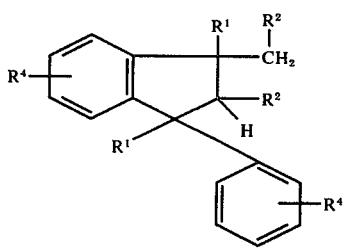

where $R^1$, $R^2$ and $R^3$ each is $C_1$ to $C_4$ alkyl or hydrogen and $R^4$ is halogen, which process comprises:

reacting as the sole starting materials to be dimerized and cyclized

A. a mixture of styrene of the formula

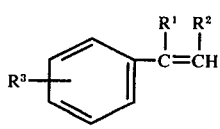

and a halogenostyrene of the formula

B. a halogenostyrene of the formula

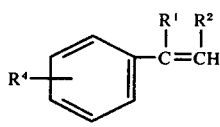

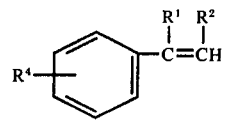

in which $R^1$, $R^2$, $R^3$ and $R^4$ have the above meanings, in a phosphoric acid of a strength of at least 75 per cent by weight and additionally in the presence of a compound which has been activated by irradiation with light of 2,000 to 8,000 A and is capable of absorbing said light, said light-activated compound being selected from the group consisting of thiourea, methylthiourea, phenylthiourea, N,N-diphenylthiourea, N,N'-diphenylthiourea, N-methyl-N-(p-toluyl)-thiourea, S-benzyl-N-phenylisothiouronium picrate, S-methyl-dithiobiuret hydrochloride, phenylmethylthiourea, 2,4-dimethoxyphenylthiourea, 4-methoxy-phenylthiourea, di-n-butylthiourea, 1-benzoyl-thiosemicarbazide, dithiobiuret, hydroquinone monomethyl ether, 4-butyl-pyrocatechol, N-benzyl-p-aminophenol, o-aminophenol, 2-mercaptobenzimidazole, 2-mercapto-4-anilinoquinazoline, 2-thiocyanomethylbenzimidazole, phenothiazine, thionaphthene, 2-mercaptobenzthiazole, 2-aminobenzthiazole, 3-aminobenzisothiazole, 2-methylbenzthiazole, diphenylenesulfide, 2,5-dimercapto-1,3,4-thiadiazole, thianthrene, leuco-methylene blue, tetramethylenetrithione, diphenylamine, m-acetaminodiphenylamine, N-phenyl-α-naphthylamine, N-phenyl-β-naphthylamine, p-isopropylamino-diphenylamine, aromatic hydrazines, o-, p- and m-nitrosophenol, N-nitrisophenylhydroxylamine ammonium salt (cupferron), nitrogen monoxide, dinitrogen tetroxide, triphenylphosphine, triphenylphosphite, thiocarboxylic acid amides, thioacetamide, anthranilic acid thiamide, 2-amino-5-nitrothiobenzamide, 2-amino-3-bromo-5-nitrothiobenzamide, 2-amino-3,5-dibromothiobenzamide, thiobenzamide, nitrobenzene, m-dinitrobenzene, m-nitroaniline, m-nitrophenol, nitroanthraquinone, p-benzoquinone, anthraquinone, 2,3,4,5-tetramethylquinone, toluquinone, chloranil, naphthoquinone and benzophenone.

2. A process as claimed in claim 1, wherein a mixture of styrene of the formula

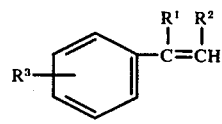

and of halogenostyrene of the formula

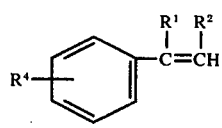

in which $R^1$, $R^2$, $R^3$ and $R^4$ have the above meanings is reacted in the presence of phosphoric acid of at least 75 per cent strength by weight.

3. A process as claimed in claim 1, wherein a mixture of styrene of the formula

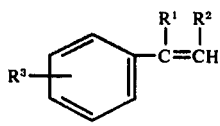

and of halogenostyrene of the formula

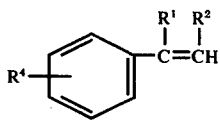

in which $R^1$, $R^2$, $R^3$ and $R^4$ have the above meanings is reacted in the presence of phosphoric acid of at least 75 per cent strength by weight and, additionally to the acid, in the presence of said organic compound irradiated with light of 2,000 to 8,000 A and capable of absorbing the said light.

4. A process as claimed in claim 1, wherein halogenostyrenes of the formula

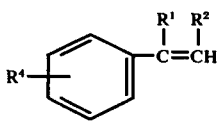

in which $R^1$, $R^2$ and $R^4$ have the above meanings are used as the sole starting materials and are reacted in the presence of phosphoric acid of at least 75 per cent strength by weight, and, additionally to the acid, in the presence of said organic compound irradiated with light of 2,000 to 8,000 A and capable of absorbing the said light.

5. A process as claimed in claim 1, wherein the reaction is carried out with 85 to 100 per cent strength by weight phosphoric acid.

6. A process as claimed in claim 1, wherein the reaction is carried out with 90 to 100 per cent strength by weight phosphoric acid.

7. A process as claimed in claim 1, wherein the reaction is carried out in the presence of additional Lewis acids or strong proton acids.

8. A process as claimed in claim 1, wherein the reaction is effected at a temperature from 10° to 150° C.

9. A process as claimed in claim 1, wherein the reaction is effected at a temperature from 20° to 50° C if a starting material II and starting material III are involved.

10. A process as claimed in claim 1, wherein the reaction is effected at a temperature from 40° to 80° C if only a starting material III is involved.

11. A process as claimed in claim 1, wherein the reaction is effected in the presence of solvents which are inert to the reaction, and are used in amounts of 50 to 150 per cent by weight based on starting material III.

12. A process as claimed in claim 1, wherein the reaction is effected in the presence of a polymerization inhibitor.

13. A process as claimed in claim 1, wherein the reaction is effected in the presence of $10^{-5}$ to $10^{-2}$ mole of polymerization inhibitor or light-absorbing compound per 1 mole of starting material III.

* * * * *